(12) United States Patent
Bergersen

(10) Patent No.: US 8,133,050 B2
(45) Date of Patent: Mar. 13, 2012

(54) DENTAL APPLIANCE HAVING A DUPLICATED TOOTH AREA AND/OR A PREDICTED TOOTH AREA AND A METHOD FOR CORRECTING THE POSITION OF THE TEETH OF A PATIENT

(75) Inventor: Earl O. Bergersen, Dorado, PR (US)

(73) Assignee: Ortho-Tain, Inc, Bayamon, PR (US)

( * ) Notice: Subject to any disclaimer, the term of this patent is extended or adjusted under 35 U.S.C. 154(b) by 1382 days.

(21) Appl. No.: 10/449,312

(22) Filed: May 30, 2003

(65) Prior Publication Data

US 2003/0224314 A1 Dec. 4, 2003

Related U.S. Application Data

(60) Provisional application No. 60/384,315, filed on May 30, 2002.

(51) Int. Cl.
*A61C 3/00* (2006.01)
(52) U.S. Cl. .......................................................... 433/6
(58) Field of Classification Search ................ 433/6, 24; 128/861
See application file for complete search history.

(56) References Cited

U.S. PATENT DOCUMENTS

| | | | |
|---|---|---|---|
| 3,724,075 A | 4/1973 | Kesling | |
| 3,837,081 A | 9/1974 | Kesling | |
| 4,073,061 A | 2/1978 | Bergersen | |
| 4,105,032 A | 8/1978 | Blomstedt | |
| 4,139,944 A | 2/1979 | Bergersen | 32/14 D |
| 4,370,129 A | 1/1983 | Huge | |

(Continued)

FOREIGN PATENT DOCUMENTS

WO PCT/US03/016733 5/2003

OTHER PUBLICATIONS

International Preliminary Examination Report for PCT/US03/16733 mailed Oct. 6, 2004.

(Continued)

*Primary Examiner* — Ralph Lewis
(74) *Attorney, Agent, or Firm* — Patents+TMS, P.C.

(57) ABSTRACT

A dental appliance and a method for correcting the arch shape and/or size of a patient by utilizing existing tooth shapes and sizes are provided. A method for correcting the position of the arch and/or teeth of a person is also provided either by a computer program or manually. Also provided is a method for correcting the position of teeth in the mouth, erupting teeth and/or teeth expected to erupt by utilizing existing tooth shapes and sizes and/or group standards. The dental appliance may be formed manually from altered models of the patient or may be formed from models made by stereolithography from a computer image. Further, the dental appliance may be made directly from laser-scanned models by stereolithography. Further, the dental appliances may have teeth sockets which may accept either a single tooth or multiple teeth. The teeth sockets may be formed to match the corresponding tooth of the patient identically or may be formed to correct the position of the tooth into the proper location. The teeth sockets may be sized based on predictions of the size and/or shape of the teeth which have not erupted. In addition, a series of appliances may be used to correct and/or guide the teeth of a patient into the proper location over a prolonged period of time. The dental appliance may correct, for example, rotations, spacing, crowding, overjet and/or overbite.

48 Claims, 7 Drawing Sheets

U.S. PATENT DOCUMENTS

| | | | | |
|---|---|---|---|---|
| 4,371,336 | A | 2/1983 | Hilleman | |
| 4,396,373 | A | 8/1983 | Dellinger | |
| 4,568,280 | A | 2/1986 | Ahlin | |
| 4,591,341 | A | 5/1986 | Andrews | |
| 4,784,605 | A | 11/1988 | Bergersen | |
| 4,799,884 | A | 1/1989 | Bergersen | 433/6 |
| 4,830,612 | A | 5/1989 | Bergersen | |
| 4,898,535 | A | 2/1990 | Bergersen | |
| 4,919,612 | A | 4/1990 | Bergersen | |
| 4,983,334 | A | 1/1991 | Adell | |
| 4,986,751 | A | 1/1991 | Bergersen | |
| 5,028,231 | A | 7/1991 | Hall | |
| 5,037,294 | A | 8/1991 | Bergersen | |
| 5,037,295 | A | 8/1991 | Bergersen | |
| 5,042,506 | A | 8/1991 | Liberati | |
| D323,215 | S | 1/1992 | Bergersen | |
| 5,194,004 | A * | 3/1993 | Bergersen | 433/215 |
| 5,203,695 | A * | 4/1993 | Bergersen | 433/6 |
| 5,328,362 | A | 7/1994 | Watson et al. | |
| 5,334,218 | A | 8/1994 | Johnson | |
| 5,338,190 | A | 8/1994 | Tregillis | |
| 5,645,420 | A | 7/1997 | Bergersen | |
| 5,683,244 | A | 11/1997 | Truax | |
| 5,779,470 | A | 7/1998 | Kussick | |
| 5,814,074 | A | 9/1998 | Branam | |
| 5,816,799 | A | 10/1998 | Parker | |
| 5,876,199 | A | 3/1999 | Bergersen | 433/6 |
| 5,911,576 | A | 6/1999 | Ulrich et al. | |
| 5,975,893 | A | 11/1999 | Chishti et al. | |
| 6,129,084 | A | 10/2000 | Bergersen | |
| 6,299,440 | B1 | 10/2001 | Phan et al. | |
| 6,454,565 | B2 | 9/2002 | Phan et al. | |
| 6,505,625 | B1 | 1/2003 | Uenishi | |
| 6,582,225 | B1 * | 6/2003 | Bergersen | 433/2 |
| 6,626,664 | B1 * | 9/2003 | Bergersen | 433/6 |

OTHER PUBLICATIONS

Search Report for PCT/US03/16733 mailed Feb. 27, 2004.

* cited by examiner

FIG. 2A
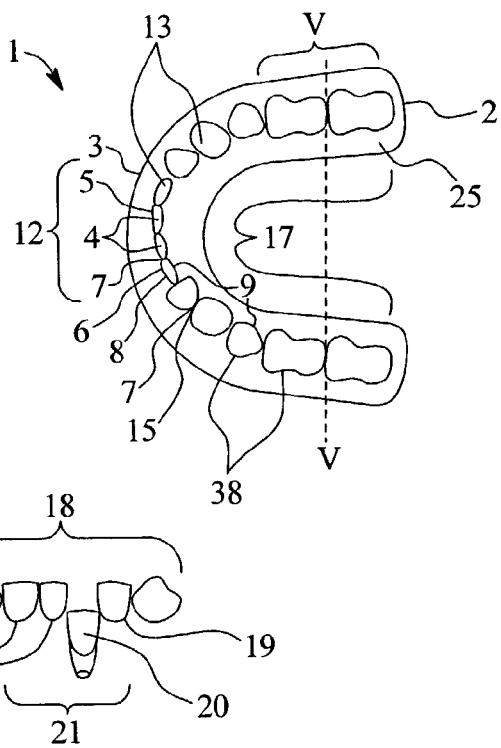
FIG. 2B
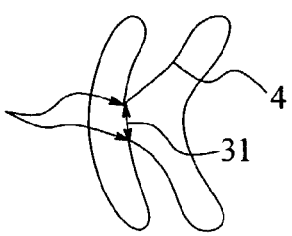
FIG. 2C
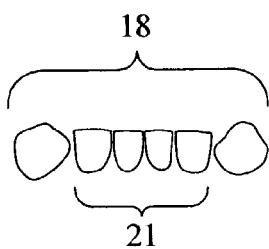
FIG. 2D
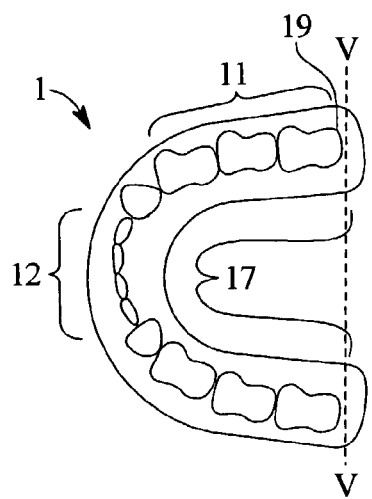
FIG. 2E

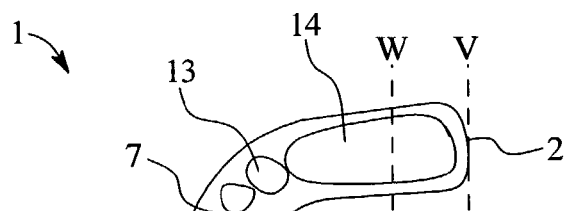
FIG. 4A
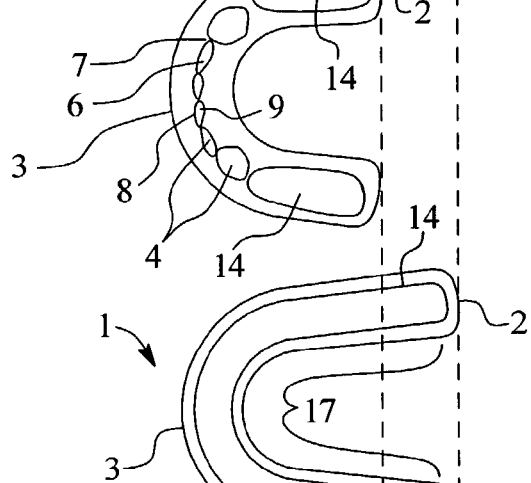
FIG. 4B
FIG. 4C
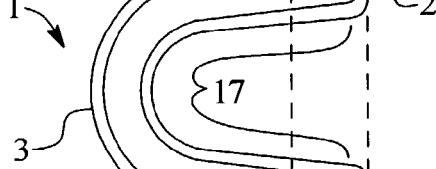
FIG. 4D
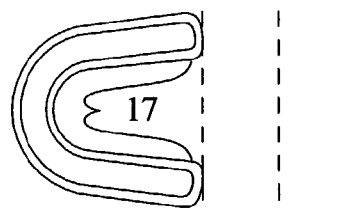
FIG. 4E
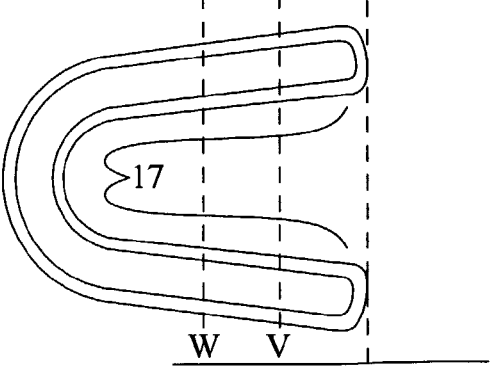

FIG. 5D

DENTAL APPLIANCE HAVING A DUPLICATED TOOTH AREA AND/OR A PREDICTED TOOTH AREA AND A METHOD FOR CORRECTING THE POSITION OF THE TEETH OF A PATIENT

This application claims the benefit of U.S. Provisional Application Ser. No. 60/384,315, filed May 30, 2002.

BACKGROUND OF THE INVENTION

The present invention generally relates to a dental appliance for correcting the position of the teeth of a patient and a method for using the same. In addition, the invention relates a method for correcting an arch of the patient. More specifically, the appliance has a duplicated tooth area and/or a predicted tooth area. The dental appliance may be generated by a computer and may duplicate the location of the teeth of the patient and/or may predict the location size and shape of the teeth for the patient. As a result, the dental appliance may simplify the treatment time and/or effort of a dentist and/or orthodontist. The dental appliance may also eliminate and/or reduce appliance adjustments, follow-up appointments and/or fees associated with other corrective dental appliances and methods.

It is generally known to provide dental care to a patient. Typically, the patient may visit, for example, a dentist or other type of care provider at the office of the care provider. The dentist, for example, may then examine the patient using various techniques, including x-raying the area to be treated or other image-taking techniques. The dentist may then provide the patient with a dental appliance to treat the condition of the patient. For example, the dental appliance may correct defects of the teeth with which an individual may be born or develop at later ages, such as an overbite, overjet, crowding, and/or spacing of teeth. The need for corrective measures for teeth has brought about various procedures, examinations, diagnoses and the like, such as those provided by a dentist or orthodontist, as well as corrective measures in the form of dental appliances which may be worn in the mouth.

However, the amount of time required by the dentist or orthodontist to create and/or adjust dental appliances is often considerable. Additionally, a cost associated with creating and adjusting these dental appliances may be considerable.

A need, therefore, exists for an improved appliance and a method for correcting the position of the teeth and/or arch of the patient. In addition, a need exists for a dental appliance and a method for creating a corrective dental appliance which may have a duplicated tooth area and/or a predicted tooth area.

In addition, a need exists for a dental appliance and a method for creating a corrective dental appliance that may be used by a person of any age, including a growing child. In addition, a need exists for a dental appliance and a method for creating a dental appliance which may be used while both deciduous and/or permanent teeth are present and/or erupting in the mouth.

SUMMARY OF THE INVENTION

According to a first aspect of the invention, a U-shaped dental appliance for correcting a malocclusion is provided comprising a duplicated tooth area which suppresses movement of a certain tooth or certain teeth and a predicted tooth area, which allows or guides tooth movement of another tooth or other teeth wherein the duplicated tooth area comprises a tooth socket or sockets made of stiff material and the predicted tooth area comprises a tooth socket or sockets made of soft material. Advantageously, the soft material is rubber.

The U-shaped dental appliance according to the invention may advantageously comprise lateral tabs for advancing the lower jaw and/or increasing the growth of the lower jaw.

Further advantageously, the U-shaped dental appliance according to the invention may additionally comprise an elevated labial shield for encouraging advancement of the lower jaw.

Preferably, the one or more of the tooth sockets in the duplicated tooth and/or the multiple tooth area of the present dental appliance are multiple tooth slots.

According to a second aspect of the present invention, a kit is provided comprising at least two U-shaped dental appliances for correcting a malocclusion, each or every dental appliance comprising a duplicated tooth area which suppresses movement of a certain tooth or certain teeth and a predicted tooth area, which allows or guides tooth movement of another tooth or other teeth, wherein the duplicated tooth area comprises a tooth socket or sockets made of stiff material and the predicted tooth area comprises a tooth socket or sockets made of soft material.

According to a third aspect of the invention, a method of generating dental appliances for converting a dental malocclusion into a corrected occlusion is provided, the method comprising the steps of:
  (a) taking a model of the upper and lower teeth of a patient;
  (b) producing a 3-D digital documentation of the patient's bite based upon the model;
  (c) generating an ideal 3-D digital model of the corrected occlusion; and
  (d) generating one or more dental appliances suitable for sequentially converting the malocclusion into the corrected occlusion according to the ideal 3-D digital model;
wherein at least one of the one or more dental appliances is a U-shaped dental appliance comprising a duplicated tooth area which suppresses movement of a certain tooth or certain teeth and a predicted tooth area, which allows or guides tooth movement of another tooth or other teeth, wherein the duplicated tooth area comprises a tooth socket or sockets made of stiff material and the predicted tooth area comprises a tooth socket or sockets made of soft material.

Preferably, according to this method, step (d) comprises the sub-steps of (d1) generating one or more resin models and (d2) generating one or more dental appliances from the one or more graduated resin models. Advantageously, the resin models and/or the graduated dental appliances are generated by stereolithography, though they may be generated manually.

Advantageously step (b) of the method according to the third aspect of the invention comprises taking a laser scan of the model to produce the 3-D digital documentation.

According to a fourth aspect of the invention, a method of converting a malocclusion in the mouth of a patient, particularly a child with deciduous, mixed or adult dentition, into a corrected occlusion, is presented, comprising the steps of
  (a) taking a model of the upper and lower teeth of a patient;
  (b) producing a 3-D digital documentation of the patient's bite based upon the model;
  (c) generating an ideal 3-D digital model of the corrected occlusion;
  (d) generating one or more dental appliances suitable for sequentially converting the malocclusion into the corrected occlusion according to the ideal 3-D digital model; and (e) sequentially fitting the one or more U-shaped dental appliances to the teeth of the patient, wherein at least one or the one or more dental appliances comprises a duplicated tooth area which suppresses movement of a certain tooth or certain teeth and a predicted tooth area, which allows or guides tooth movement of another tooth or other teeth and wherein the duplicated tooth area comprises a tooth socket or sockets made of stiff material and the predicted tooth area comprises a tooth socket or sockets made of soft material.

Advantageously, step (e) of the method comprises the steps of sequentially fitting two or more U-shaped dental appliances to the teeth of the patient, such that each successive U-shaped dental appliance gradually corrects the occlusion, the last U-shaped dental appliance in the sequence completing correction of the occlusion.

More advantageously, the method according to the fourth aspect of the invention includes correction of the arch of the teeth of the patient by providing U-shaped dental appliances having an arch different from the patient's natural arch.

Preferably, according to the fourth aspect of the invention, the step of generating the ideal digital model of the corrected occlusion comprises the step of estimating the sizes and shapes of non-erupted teeth, wherein the estimation is based upon the sizes and shapes of pre-erupted permanent teeth or upon an x-ray radiograph of the patient's mouth.

In addition, step (b) preferably comprises taking a laser scan of the model to produce the 3-D digital documentation.

According to a fifth aspect of the invention a method of converting a malocclusion in the mouth of a patient, particularly a child with deciduous dentition, into a corrected occlusion, is presented, comprising the steps of
 (a) taking a model of the upper and lower teeth of a patient;
 (b) producing a 3-D digital documentation of the patient's bite based upon the model;
 (c) generating an ideal 3-D digital model of the corrected occlusion;
 (d) generating one or more dental appliances suitable for sequentially converting the malocclusion into the corrected occlusion according to the ideal 3-D digital model;
 (e) sequentially fitting the one or more U-shaped dental appliances to the teeth of the patient, wherein at least one or the one or more dental appliances comprises at least one multiple tooth slot.

Advantageously, one of the one or more multiple tooth slots is designed to fit the second bicuspid and the first permanent molar, the first and second deciduous molars and the first permanent molar, or the first and second deciduous molars of a patient.

Advantageously, step (b) of the method according to the fifth aspect of the invention comprises taking a laser scan of the model to produce the 3-D digital documentation.

Further, in an embodiment of the present invention, a dental appliance is provided which is worn adjacent to teeth in a mouth of a user. The dental appliance has a generally U-shaped base wherein the base is sized to receive one or more teeth of the user and further wherein the base is shaped to receive a predicted size of one of the teeth of the user which has not erupted.

In an embodiment, the dental appliance has a socket within the base wherein the socket is shaped to receive at least one of the teeth of the user In an embodiment, the base is constructed from a first material and a second material wherein the first material is softer than the second material.

In an embodiment, the dental appliance has a shield integrally formed with the base wherein the teeth contact the shield.

In another embodiment of the present invention, a dental appliance is provided which is worn adjacent to teeth in a mouth of a user. The dental appliance has a generally U-shaped base having a length defined between a first end and a second end and further having a top surface and a bottom surface wherein the base is sized to receive one or more teeth of a user and further wherein a first portion of the base is shaped based on a predicted size of one or more teeth of the user which have not erupted and a second portion of the base is shaped based on a size of one or more teeth of the user which have erupted.

In an embodiment, the dental appliance has a tab integrally formed with the base wherein the tab extends toward the mouth.

In an embodiment, a distance between the top surface and the bottom surface at the first end is greater than a distance between the top surface and the bottom surface at the second end.

In an embodiment, the base is constructed from a plurality of materials having different degrees of rigidity.

In an embodiment, the dental appliance has a socket within the base wherein the socket has a flat occlusal surface.

In an embodiment, the dental appliance has a rib formed within the base wherein the rib contacts at least one tooth and causes rotation of the tooth.

In an embodiment, the dental appliance has a socket within the base wherein the socket is sized to receive at least two teeth of the user.

In another embodiment of the present invention, a dental appliance is provided which is worn adjacent to teeth in a mouth of a user. The dental appliance has a generally U-shaped base generated by a computer and sized to receive one or more teeth of a user wherein the size of the base is predicted based on one or more teeth of the user which have not erupted.

In an embodiment, the dental appliance has a socket within the base wherein the socket is sized to receive at least two of the teeth of the user.

In an embodiment, the dental appliance has a shield integrally formed with the base wherein the shield covers the teeth.

In an embodiment, the base is constructed from a first material and a second material wherein the first material is softer than the second material.

In an embodiment, the dental appliance has a socket within the base wherein the socket is shaped to coincide with one of the teeth of the user.

In an embodiment, the dental appliance has a plurality of ribs formed within the base wherein the plurality of ribs contact at least two of the teeth and causes rotation of the teeth.

In an embodiment, the dental appliance has a tab integrally formed with the base wherein the tab has an apex.

In another embodiment of the present invention, a dental appliance is provided which is worn adjacent to teeth in a mouth of a user. The dental appliance has a generally U-shaped base sized to receive one or more teeth of a user wherein the base contains sockets for receiving one or more teeth and wherein a size of each of the sockets is computer-generated based on a predicted size of one or more incisors of the user which have not erupted.

In an embodiment, the dental appliance has a shield integrally formed with the base wherein the shield has a shape which corresponds to a shape of the mouth.

In an embodiment, the dental appliance has a tab integrally formed with the base wherein the tab extends toward the mouth of the user.

In an embodiment, the dental appliance has a rib formed within the base wherein the rib contacts one of the teeth and causes rotation of the tooth.

In an embodiment, one of the sockets within the base has a flat occlusal surface.

In an embodiment, at least two of the sockets are constructed from materials of differing rigidity.

In another embodiment of the present invention, a dental appliance is provided which is worn adjacent to teeth in a mouth of a user. The dental appliance has a generally U-shaped base sized to receive one or more teeth of a user wherein the base has a perimeter. The dental appliance also has a wall extending along the perimeter of the base wherein the base and the wall are shaped to receive a tooth which has not erupted and wherein the base and the wall are sized based on a size of one or more erupted permanent teeth.

In an embodiment, the dental appliance has a rib formed within the base adjacent to the wall wherein the rib causes rotation of the teeth.

In an embodiment, the dental appliance has a socket within the base wherein the socket is shaped to receive at least one of the teeth of the user.

In an embodiment, the dental appliance has a tab integrally formed with the base wherein the tab extends into the mouth.

In an embodiment, the dental appliance has a socket within the base wherein the socket receives at least two of the teeth of the user and has a flat occlusal surface.

In an embodiment, the dental appliance has the base is constructed from a first material and a second material wherein the first material is softer than the second material.

In another embodiment of the present invention, a dental appliance is provided which is worn adjacent to teeth in a mouth of a user. The dental appliance has a generally U-shaped base sized to receive one or more of the teeth of the user. The dental appliance also has sockets within the base wherein the sockets are sized to receive teeth of the user which have not erupted wherein the size of one of the sockets is based on an image of an interior of a mouth of the user.

In an embodiment, the image is an X-ray image.

In an embodiment, the image is a digital image.

In an embodiment, the sockets are constructed from materials having differing rigidities In an embodiment, the dental appliance has a rib formed within the socket wherein the rib moves the teeth.

In another embodiment of the present invention, a dental appliance is provided which is worn adjacent to teeth in a mouth of a user. The dental appliance has a generally U-shaped base sized to receive one or more teeth in the mouth of a user. In addition, the dental appliance has a first socket within the base wherein the first socket is sized to receive a single tooth of the user which has not erupted based on a predicted size of the single tooth. Further, the dental appliance has a second socket within the base wherein the second socket is sized to receive two or more teeth of the user.

In an embodiment, the dental appliance has a tab integrally formed with the base wherein the tab extends toward the mouth of the user In an embodiment, the dental appliance has a shield integrally formed with the base wherein the shield covers the teeth.

In an embodiment, the base is constructed from a first material and a second material wherein the first material is softer than the second material.

In another embodiment of the present invention, a dental appliance is provided which is worn adjacent to teeth in a mouth of a user. The dental appliance has a generally U-shaped base sized to receive teeth in a mouth of a user. The dental appliance also has a socket within the base wherein the socket has walls defining an interior and is shaped to receive one or more teeth of the user and wherein the socket has a rib formed within the walls of the socket wherein the rib causes rotation of the teeth.

In an embodiment, the size of the base is based on a predicted size of a tooth which has not erupted.

In an embodiment, the dental appliance has a tab integrally formed with the base wherein the tab has an apex.

In an embodiment, the dental appliance has the base is constructed from a first material and the socket is constructed from a second material wherein the first material is softer than the second material In an embodiment, the dental appliance has a shield integrally formed with the base wherein the teeth contact the shield.

In another embodiment of the present invention, a dental appliance is provided which is worn adjacent to teeth in a mouth of a user. The dental appliance has a generally U-shaped base. The dental appliance also has a first socket within the base wherein the first socket is shaped to correspond to a shape of one of the teeth of the user. Further, the dental appliance has a second socket within the base wherein the second socket is sized to receive two or more teeth of the user wherein the second socket has a flat surface which contacts the teeth and wherein either the first socket or the second socket is sized based on a predicted size of at least one tooth of the user which has not erupted.

In an embodiment, the first socket is constructed from a first material and the second socket is constructed from a second material wherein the first material is softer than the second material.

In an embodiment, the base is constructed from a first material and the first socket is constructed from a second material wherein the first material and the second material have a different rigidity.

In an embodiment, the dental appliance has a rib formed within the first socket wherein the rib contacts the tooth and causes rotation of the tooth.

In another embodiment of the present invention, a dental appliance is provided which is worn by a user having anterior teeth and posterior teeth in a mouth of the user. The dental appliance has a generally U-shaped base wherein the base is sized based on a predicted size of one or more teeth which have not erupted and wherein the base contacts the anterior teeth of the user and wherein the base does not contact one of the posterior teeth of the user.

In an embodiment, the dental appliance has a socket within the base wherein the socket receives at least one tooth of the user.

In an embodiment, the dental appliance has a shield integrally formed with the base wherein the shield is constructed from a first material and the base is constructed from a second material wherein the first material is softer than the second material.

In an embodiment, the dental appliance has a socket within the base wherein the socket is shaped to receive at least two of the teeth of the user.

In an embodiment, an area of the dental appliance that is predicted is constructed from a first material which is softer than a material used to construct a remainder of the base.

In an embodiment, the dental appliance has a tab integrally formed with the base wherein the tab has an apex.

In an embodiment, the dental appliance has a rib formed within the base wherein the rib contacts one or more of the anterior teeth and causes rotation of the anterior teeth.

In another embodiment of the present invention, a dental appliance is provided which is worn adjacent to teeth in a mouth of a user. The dental appliance has a generally U-shaped base having an inside perimeter and an outside perimeter. The dental appliance also has a wall extending from the base along the outside perimeter wherein the wall has a surface and wherein the wall has one or more protrusions extending from the surface wherein the protrusions contact a lip of the user.

In an embodiment, the dental appliance has a tab integrally formed with the base wherein the tab extends toward the mouth of the user.

In an embodiment, the dental appliance has a rib formed within the base wherein the rib contacts a tooth and moves the tooth.

In an embodiment, the dental appliance has a socket within the base wherein the socket is shaped to receive one of the teeth of the user.

In an embodiment, the dental appliance has a socket within the base wherein the socket is shaped to receive at least two of the teeth of the user.

In an embodiment, the base is sized based on a predicted size of a tooth which has not erupted.

In an embodiment, the base is constructed from a first material and the wall is constructed from a second material wherein the first material is softer than the second material.

In another embodiment of the present invention, a sheet is provided for treating a malocclusion of a user having teeth. The sheet has a first portion wherein the first portion is constructed from a first material. The sheet also has a second portion wherein the second portion is constructed from a second material wherein the first material is softer than the second material and further wherein the sheet is molded into a dental appliance for treating the malocclusion wherein the first material contacts teeth requiring correction and wherein the second material contacts teeth which do not require correction.

In an embodiment, the first portion has a first thickness and the second portion has a second thickness wherein the first thickness is not equal to the second thickness.

In an embodiment, the first portion is molded into a predicted shape of a tooth which has not erupted.

In another embodiment of the present invention, a system is provided for treating a malocclusion. The system has a first dental appliance worn in the mouth of a user having the malocclusion wherein a portion of the first dental appliance is shaped based on a predicted size of one or more teeth of the user which have not erupted. The system also has a second dental appliance worn in the mouth of the user after the user wears the first dental appliance wherein a portion of the second dental appliance is shaped in correlation to teeth partially corrected by the first dental appliance.

In an embodiment, the second dental appliance is sized based on a predicted size of one or more teeth of the user.

In an embodiment, the system has a computer wherein a model of the first dental appliance is generated by the computer.

In an embodiment, the system has a computer wherein a model of the second dental appliance is generated by the computer.

In another embodiment of the present invention, a method is provided for correcting a position of teeth of a patient. The method comprises the steps of: obtaining a model of the teeth of the patient; scanning the model to provide a digital model; diagnosing a malocclusion based on the digital model; and designing a series of dental appliances to be worn to treat the malocclusion.

In an embodiment, the method further has the step of manufacturing the series of dental appliances.

In an embodiment, the method further has the step of fitting one of the series of dental appliances onto the teeth of the patient on an upper occlusion and a lower occlusion.

In an embodiment, the method further has the step of providing the series of dental appliances to the patient.

In an embodiment, the diagnosis is performed by a computer.

In an embodiment, the method further has the step of rearranging the teeth in the digital model of the patient to provide an ideal dentition after diagnosing the malocclusion.

It is, therefore, an advantage of the present invention to provide a dental appliance and a method for correcting the position of the teeth of a patient.

A further advantage of the present invention is to provide a dental appliance and a method for correcting the position of a single tooth of a patient.

A further advantage of the present invention is to provide a dental appliance and a method for correcting an occlusal bite of a patient.

It is a further advantage of the present invention to provide a dental appliance and a method for correcting an arch of a patient.

It is yet another advantage of the present invention to provide a dental appliance and a method for correcting the arch of a patient by using a computer generated program.

It is yet another embodiment of the present invention to provide a dental appliance and a method for correcting the position of one or more teeth of a person of any age.

It is yet another embodiment of the present invention to provide a dental appliance and a method for correcting the position of teeth of a person while permanent and/or deciduous teeth are present and/or erupting in the mouth.

It is yet another embodiment of the present invention to provide a dental appliance and a method for correcting the position of teeth of a person by guiding the erupting teeth into a desired position in the mouth.

It is further an advantage of the present invention to provide a dental appliance and a method which corrects the teeth in a short amount of time.

It is further an advantage of the present invention to provide a method for correcting the teeth of a patient which requires only one or a few dental appliances.

Another advantage of the present invention is to provide a dental appliance and a method for correcting the teeth of a patient wherein the appliance reduces the amount of time required for creating the dental appliance.

Yet another advantage of the present invention is to provide a dental appliance and a method for correcting the teeth of a patient wherein the dental appliance reduces an expense associated with obtaining the corrective dental appliance.

Still another advantage of the present invention is to provide a dental appliance and a method for correcting the teeth of a patient which is appealing to the public.

Further, an advantage of the present invention is to provide a dental appliance and a method for correcting the teeth of a patient which requires few, if any, adjustments and/or few, if any, appointments by a dentist or orthodontist.

Additional features and advantages of the present invention are described in, and will be apparent from, the detailed description of the presently preferred embodiments and from the drawings.

BRIEF DESCRIPTION OF THE DRAWINGS

FIG. 2A illustrates top plan view of an appliance in an embodiment of the present invention.

FIG. 2B illustrates a front view of the tooth arrangement of a lower anterior segment.

FIG. 2C illustrates a cross section view of the front of the dental appliance in an embodiment of the present invention.

FIG. 2D illustrates a top plan view of an appliance in an embodiment of the present invention.

FIG. 2E illustrates four predicted sizes and/or shapes of the lower permanent incisors.

FIG. 4A illustrates a top perspective view of a corrective dental appliance having slots for multiple teeth after the first permanent molars have erupted in a six to eleven year old in an embodiment of the present invention.

FIG. 4B illustrates a top plan view of another embodiment of a corrective dental appliance having slots for multiple teeth before the first permanent molars have erupted in a youth under the age of six in an embodiment of the system of the present invention.

FIG. 4C illustrates a top plan view of a dental appliance having one slot for multiple teeth after the first permanent molars have erupted in a six to eleven year old in an embodiment of the present invention.

FIG. 4D illustrates a top plan view of a dental appliance having one slot for multiple teeth before the first permanent molars have erupted in a youth under the age of six in an embodiment of the present invention.

FIG. 4E illustrates a top plan view of a dental appliance having a multiple tooth slot after the first and second permanent molars have erupted in an individual twelve years or older in an embodiment of the present invention.

FIG. 5D illustrates a top view of the dental appliance of FIG. 5B in an embodiment of the present invention.

DETAILED DESCRIPTION OF THE PRESENTLY PREFERRED EMBODIMENTS

Figure 1:
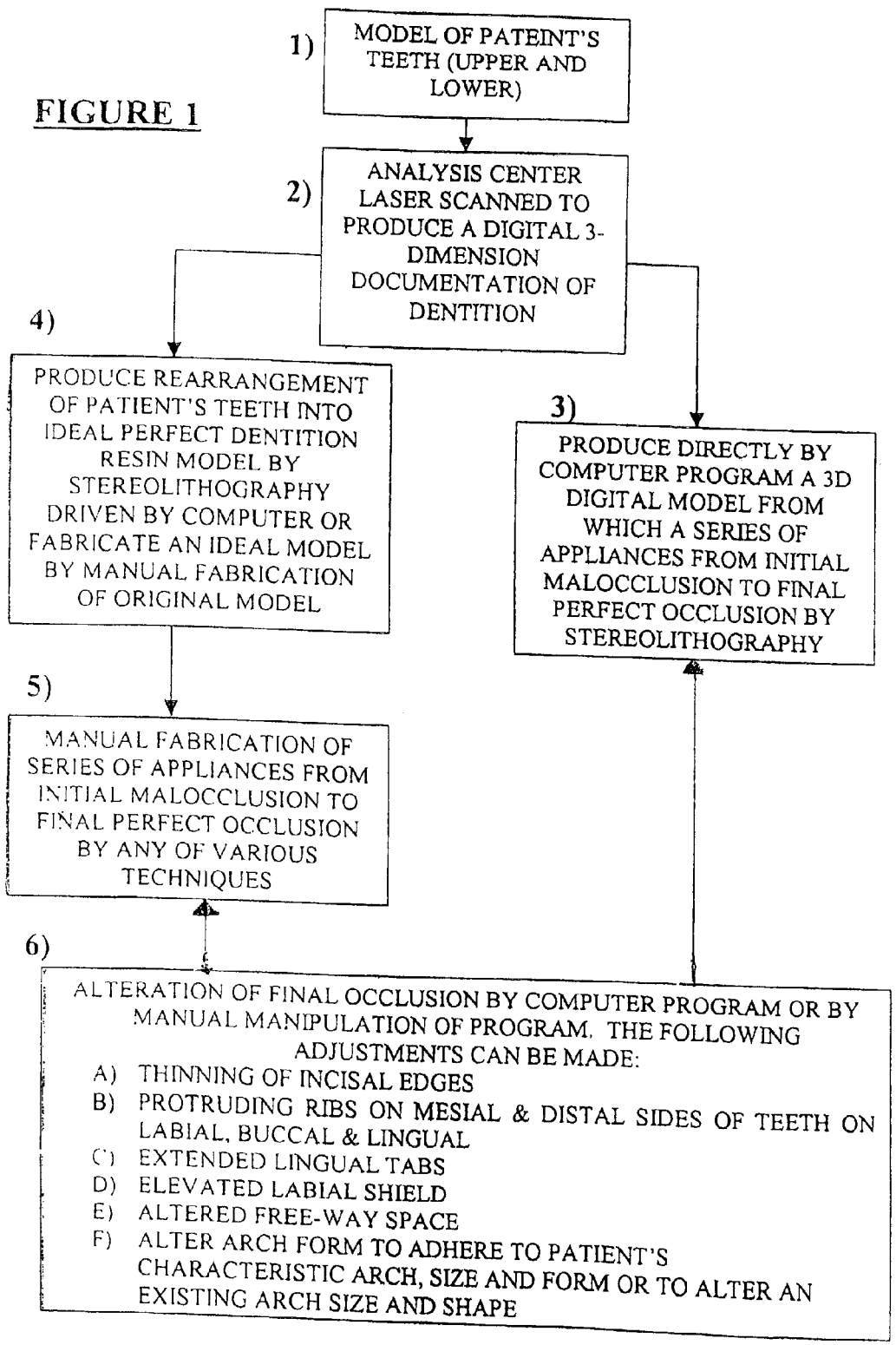
FIG. 1 illustrates a flow chart of a method for computer analysis of the teeth of a patient to create a dental appliance in an embodiment of the present invention.

The present invention relates to a dental appliance and a method for correcting the position of teeth within a mouth of a patient. The present invention further relates to a method for correcting an arch of the teeth of the patient. To this end, the dental appliance may have a duplicated tooth area and/or a predicted tooth area. The predicted tooth area may be based on, for example, a size of a mouth, a size of an arch of the patient, baby teeth of a patient, erupted teeth, or erupted baby teeth of a patient. Moreover, the dental appliance may be generated by a computer. The computer (not shown) may use any digital source, for example, laser scanned models of the teeth, digital photos or x-rays to generate a model or a digital 3-D model of the teeth of the patient for creation of the dental appliance. Alternatively, the dental appliance for straightening the teeth of the patient may be created by, for example, vacuum formation, pressure formation, stereolithography directly from a digital 3-D image of the mouth or by a like fabrication method.

By analyzing the sizes of fully erupted adult teeth, the size of unerupted or erupting teeth may be calculated, as shown in the table below. The shapes of the erupting or non-erupted teeth may be obtained from standards of average anatomic shapes of groups of teeth.

| Predicting mesio-distal sizes of adult teeth | | |
|---|---|---|
| Lateral (lower) = | Central (lower) + | 0.5 mm |
| Central (upper) = | Central (lower) + | 3.25 mm |
| Lateral (upper) = | Central (upper) + | 2.0 mm |
| Lateral (upper) = | Central (lower) + | 1.25 mm |
| Incisors (lower 4) = | Central (lower) × 4 + | 1.0 mm |
| Incisors (upper 4) = | Incisors (lower 4) + | 8.0 mm |
| Canine (upper) = | Lateral (upper) + | 1.25 mm |
| Canine (upper) = | Central (upper) − | 1.0 mm |
| Canine (upper) = | Canine (lower) + | 1.0 mm |
| Premolar = (upper $1^{st}$ or 2nd) | Central (upper) − | 1.8 mm |
| Canine (lower) = | Central (lower) + | 1.5 mm |
| $1^{st}$ Premolar (lower) = | Central (lower) + | 1.6 mm |
| $2^{nd}$ Prmolar (lower) = | Central (lower) + | 1.9 mm |
| $2^{nd}$ Permanent Premolar (upper) = | Dec. $2^{nd}$ molar (upper) − | 2.25 mm (approx) |
| $2^{nd}$ Permanent Premolar (lower) = | Dec. $2^{nd}$ molar (lower) − | 2.6 mm (approx) |
| Leeway space lower per side (canine, both premolars) = | | 2.5 mm* |
| Leeway space upper per side (canine, both premolars) = | | 1.4 mm* |
| Low. dec. canine & molars per side (male) = | | 23.55 mm |
| Low. perm. canine & premolars per side = | | 21.32 mm |
| Difference per side = 2.23 mm. MALE | | |
| Low. dec. canine & molars per side (female) = | | 23.03 mm |
| Low. perm. canine & premolars per side = | | 20.36 mm |
| Difference per side = 2.67 mm. FEMALE | | |
| Mean difference lower (male & female per side) = 2.5 mm | | |
| Upp. dec. canine & molars per side (male) = | | 23.08 mm |
| Upp. perm. canine & premolars per side = | | 21.78 mm |
| Difference per side = 130 mm MALE | | |
| Upp. dec. canine & molars per side (female) = | | 22.46 mm |
| Upp. perm. canine & premolars per side = | | 21.00 mm |
| Difference per side = 1.46 mm. FEMALE | | |
| Mean difference upper (male & female per side) = 1.4 mm | | |

*Average of Male and Female (See Moorrees, C.F.A.: *The Dentition of the Growing Child*, Harvard University Press, Cambridge, Mass, 1959.)

The average size and shape of each tooth not fully erupted in the mouth and corresponding to the varius sizes of other teeth in the mouth may be estimated from a computer program. The other teeth in the mouth may also be estimated manually using charts and various altered models of teeth.

Figure 5A:
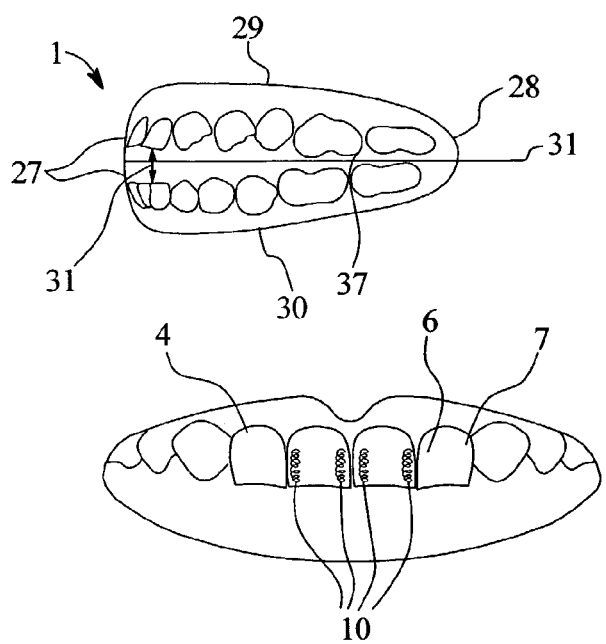
FIG. 5A illustrates a side view of a dental appliance in an embodiment of the present invention.

Referring now to figures, wherein like numbers refer to like parts, FIGS. 2A and 5A illustrate the dental appliance 1 which may have a plurality of teeth sockets 4 having an incisal edge 5 and an arch 17. The teeth sockets 4 of the dental appliance 1 may also have a mesial surface 6 and/or a distal surface 7. Further, the dental appliance 1 may have one or more protruding ribs 10. The dental appliance 1 may alter the teeth and/or orthodontically move the teeth when the incisal edges 5 of teeth sockets 4 are thinned and/or protruding ribs 10 are placed on the mesial surfaces 6 and/or the distal surfaces 7 of the teeth sockets 4. More specifically, the thinning of the teeth sockets 4 and/or the placement of the protruding ribs 10 labially and/or lingually on the teeth sockets 4 may enable efficient tooth movement. In addition, the dental appliance 1 may alter a freeway space 31 of the patient. The freeway space 31 may be seen in FIG. 5A. The freeway space 31 may define the vertical area between the upper and lower teeth all the way around the arch of the patient.

The dental appliance 1 may be based entirely on the volumetric size and shape of the teeth of the patient with modifications to only, for example, the shape and/or size of the arch 17 of the teeth of the patient. Further, the addition of the protruding ribs 10 and/or bumps mesio-distally may be the only modification. Still further, the incisal edges 5 of the teeth sockets 4 may be thinned and/or the freeway space 31 may be modified. Such changes may enhance crowding corrections as well as the overbite when more material exists in the front of the freeway space 31 than in the back of the freeway space 31. Additionally, the amount of material used may be more than the patient would normally have. As a result, the front teeth may be depressed and the back teeth may be encouraged to erupt. Further, the over-bite of the patient may be corrected.

Referring now to FIG. 1, a flow chart is provided of a computer analysis of the teeth of the patient for creating the dental appliance. More specifically, Step 1 illustrates that a model of the upper and lower teeth of the patient may be taken. Step 2 illustrates that a laser may then scan the model of the teeth to produce a 3-dimensional (3-D) digital documentation of the bite of the patient, as shown in the dental appliance 1. Formation of the corrective dental appliance 1 may proceed from Step 2 to either Step 3 or Step 4. In Step 3, the computer may create an ideal 3-D digital model of the teeth from digital data from the original model of the patient. Additionally, a dental appliance 1 or a series of sequential dental appliances 1 may be made by stereolithography based from the 3-D image. The computer may also convert the initial malocclusion of the patient into a perfect occlusion resin model(s) by stereolithography from which a dental appliance 1 or a graduated series of dental appliances 1 may be manually fabricated from a graduated series of resin models produced by, for example, stereolithography.

In Step 4, an ideal dentition may be produced manually or via the computer from the original dentition of the teeth of the patient. Following Step 4, the computer or person may proceed to Step 5. In Step 5, a series of dental appliances 1 may be created by manual fabrication for the treatment of stages of malocclusion from an initial malocclusion of the patient into a final and/or normal occlusion by various techniques.

In an alternative to proceeding to Step 4 from Step 2, the computer or person may proceed to Step 3 (as described above). At Step 3, the computer or person may alter the model(s) or digital image from which the dental appliance 1 are fabricated from by implementing step six. In Step 6, an alteration of the final occlusion may be made by a computer or by manual manipulation. Specifically, the incisal edge 5 of at least one tooth may be thinned. Thinning the incisal edge 5 of at least one tooth may enhance crowding corrections as well as correct overbites. Additionally, protruding ribs 10 may be added on the mesial side 6 and/or distal side 7 of the teeth and/or on a labial surface 8, a buccal 38 or a lingual side 9 of the teeth. The buccal surface 38 may describe the surface of the teeth facing the cheeks of the person.

Further, lingual tabs 35 may be extended to keep the lower jaw from slipping backward. The lingual tabs 35 may be seen in FIG. 7. More specifically, the lingual tabs 35 may further encourage the jaw to develop forward, thereby, correcting an excessive overjet. Additionally, a labial shield 36 may be elevated to prevent the dental appliance 1 and the lower jaw from slipping backward. The labial shield 36 may be seen in FIG. 7. As a result, the labial shield 36 may correct overjet. Still further, the freeway space 31 may be altered.

In addition, the arch 17 may be altered to adhere to the characteristics of the size and/or form of the patient or to change the arch 17 form or size if required. The arch 17 of the dental appliance 1 may also be altered by a computer. For example, the upper arch 17 may be significantly widened and rounded to coordinate with the lower arch 17 for a patient with a severe overjet and/or upper lingual cross-bite. Appendix A illustrates standards for predicting the size of non-erupted teeth.

Referring now to FIG. 2A wherein like numerals refer to like parts, FIG. 2A generally illustrates a top plan view of the dental appliance 1. The dental appliance 1 may be created by a dentist or orthodontist from information obtained regarding to the teeth of the patient. In addition, the dental appliance 1 may be created at a manufacturing facility. The dental appliance 1 may be manufactured from, for example, plastic or any other pliable material.

The dental appliance 1 may have a first end 2 and a second end 3 and may be designed by a computer. Teeth sockets 4 may be located on the dental appliance 1. The teeth sockets 4 may resemble the teeth structures of, for example, a human. More specifically, the teeth sockets 4 may have the incisal edge 5 (cutting edges), the mesial surface 6 and the distal surface 7. The mesial surface 6 of a tooth may be the surface of a tooth that is adjacent to the tooth in front of it, or closest to the front and middle of the mouth. The distal surface 7 of a tooth may be the surface of a tooth closest to the rear of the mouth. Each of the teeth sockets 4 may further have the labial surface 8, buccal surface 38 and the lingual surface 9. The labial surface 8 may describe the surface of the teeth facing the lips of a person. The lingual surface 9 may describe the surface of the teeth facing the tongue. The buccal surface 38 may describe the surface of the teeth facing the cheeks.

The arch 17 of the dental appliance 1 may be generally U-shaped and may describe the curvature of the dental appliance 1. Additionally, the arch 17 of the dental appliance 1 may vary in order to accommodate different patients using different versions of the dental appliance 1.

The dental appliance 1 may further have a duplicated tooth area 11 and/or a predicted tooth area 12 as illustrated in FIGS. 2A and 2D. Area(s) of the mouth which do not require tooth movement may be within the duplicated tooth area 11 and may, but not necessarily, resemble the present location of the teeth of the patient. Area(s) of the mouth which require tooth movement may be within the predicted tooth area 12 and may, but not necessarily, resemble a desired location of the teeth in the mouth. However, the exact location, size and shape of the desired teeth may not be based on the direct anatomy of the teeth of the patient, but may be based on group standards.

The dental appliance 1 having the predicted tooth area 12 and/or duplicated tooth area 11 may be designed by a computer. The dental appliance 1 may be designed for adjusting all of the teeth of the patient or may be designed to adjust some of the teeth of the patient. Further, the dental appliance 1 may be formed to guide the future location of the teeth of the patient or may be formed identical to the current location of the teeth of the patient, but formed to straighten the teeth. As illustrated in FIG. 2A, the dental appliance 1 may have second permanent molars distal to the V-V line. As illustrated in FIG. 2D, the dental appliance 1 may not have a second permanent molars distal to Line V-V. The dental appliance 1 or a series of dental appliances 1 may be utilized by the patient. More specifically, the series of dental appliances 1 may be produced from digital images by sterolitograph or may be produced manually with the use of a vacuum or pressure-type thermal molding technique, for example.

The duplicated tooth area 11 of the dental appliance 1 may be made of a stiff material 25 which suppresses movement of the teeth of the patient. Additionally, the duplicated tooth area 11 may adhere well to the undercuts in the mouth of the patient. The duplicated tooth area 11 of the dental appliance 1 may further be used in computerized tooth setups for the retention of the dental appliance 1 or appliances to the teeth.

The predicted tooth area 12 of the dental appliance 1 may be made of a soft material 26 which may allow tooth guidance or movement. Further, the soft material 26 may better accommodate variations in the predicted shape and/or size of the teeth. The predicted tooth area 12 may be made of, for example, rubber and may have either a predicted teeth formation or may have a formation of the anatomy of the teeth of the patient. Further, the computer may rearrange the teeth sockets 4 in the predicted tooth area 12 in order to straighten the crowding of the teeth. Additionally, the predicted tooth area 12 may be formed according to predictions of the teeth sizes and shapes of the patient and/or from group standards.

The duplicated tooth area 11 and/or the predicted tooth area 12 of the dental appliance 1 may either match the natural arch 17 of the teeth of the patient or be formed to correct the arch 17 of the teeth of the patient. The duplicated tooth area 11 and/or the predicted tooth area 12 may also contain modifications that alter jaw relations and/or functions. Additionally, the duplicated tooth area 11 and/or the predicted tooth area 12 may, for example, contain the lateral tabs 35 for advancing the lower jaw and/or increasing the growth of the lower jaw. Further, the duplicated tooth area 11 and/or the predicted tooth area 12 may, for example, contain the elevated labial shield 36, which may encourage the advancement of the lower jaw. As a result, overjet may be corrected. Further, the duplicated tooth area 11 and/or the predicted tooth area 12 may also correct overbite and/or openbite by, for example, altering of the freeway space 31 material in a front end 27 and/or a rear end 28 of the dental appliance 1.

Referring now to FIG. 2B, an anterior occlusion 18 may be computer generated based on the volumetric size of the teeth of the patient not requiring correction or eruption guidance. The computer may use the mesiodistal size 19 of the permanent teeth present to estimate the specific size of the predicted tooth area 12 for the teeth requiring eruption guidance. Further, the computer may use an x-ray to determine the size and/or shape of the unerupted teeth of a youth to estimate the specific size of the predicted tooth area 12 for the teeth requiring eruption guidance. Further, the computer may estimate the shape of the teeth requiring eruption guidance from group standards of various shapes of the teeth.

Additionally, the computer may preset the teeth in a desired anterior occlusion 18 according to, for example, the form of the arch 17. Further, the computer may preset the teeth in a desired anterior occlusion 18 according to, for example, the shape and/or size of the arch 17 of the lower and/or upper teeth of the patient.

FIG. 2B further illustrates a plurality of deciduous teeth 19 in the mouth of the patient. The deciduous teeth are the teeth which may eventually fall out of the mouth of the patient. The anterior occlusion 18 may further have a permanent lower central incisor 20 which may begin to erupt into a lower anterior segment 21 of the mouth of the patient. An area may be preset manually or by computer by predicting the sizes of the not yet erupted permanent teeth 18 as shown in FIG. 2E. FIG. 2C illustrates a cross sectional view of the dental appliance 1 wherein the incisal edges 5 of the teeth sockets 4 are visible.

Referring now to FIG. 2D, the dental appliance 1 may be used by a child. More specifically, the dental appliance 1 may be used by a child six to eleven years old. Further, the dental appliance 1 may be used by a child wherein the second permanent molars have not erupted behind the V-V line.

Referring now to FIG. 2E, four predicted sizes and/or shapes of the lower permanent incisors may be estimated manually or by the computer. More specifically, the incisors may be in a proper alignment and ready for guidance prior to eruption.

Figure 3:
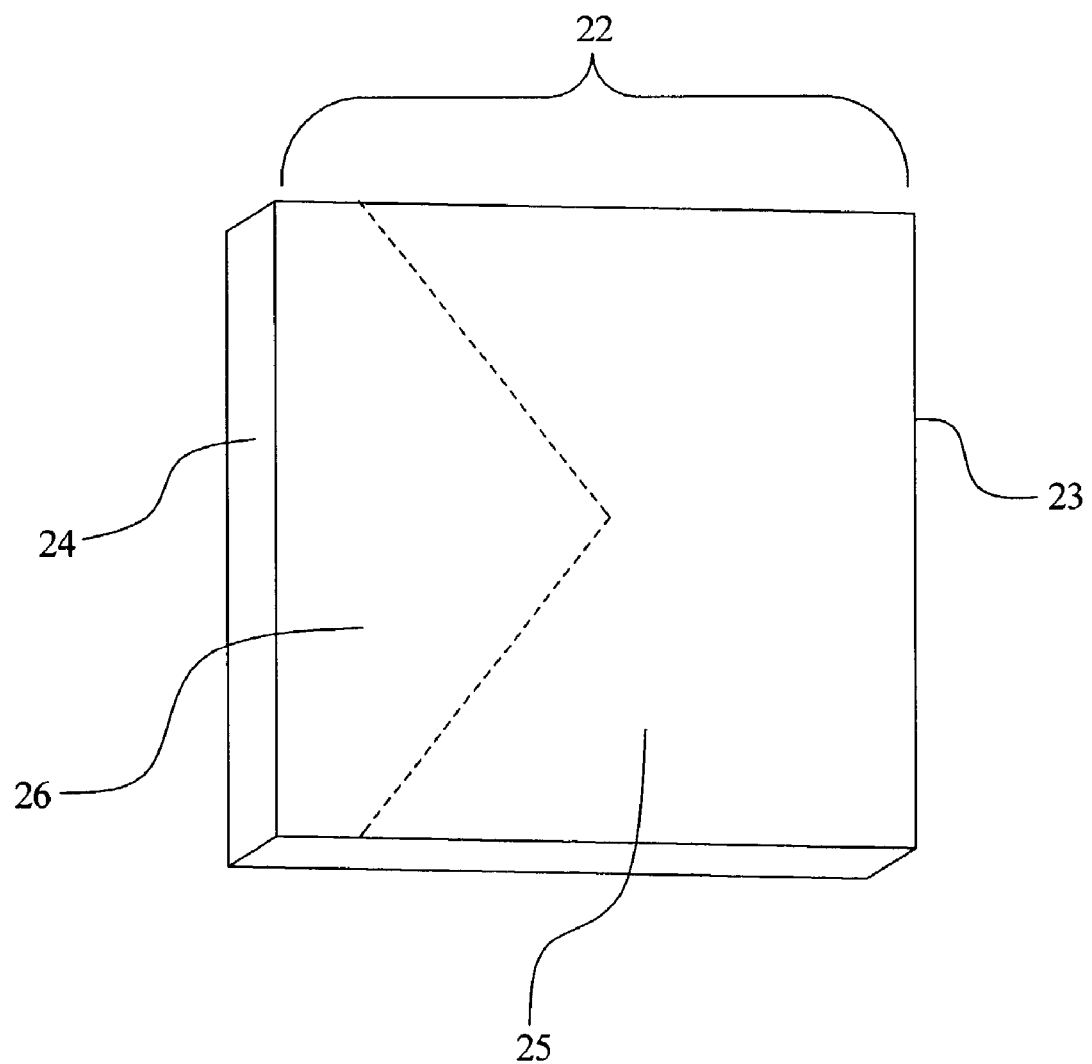
FIG. 3 illustrates a top perspective view of a sheet of thermoplastic material used to create a dental appliance in an embodiment of the present invention.

Referring now to FIG. 3, the dental appliance 1 may be produced using a molding technique, generally called Biostar (sold by Dentaurum of Germany). More specifically, the molding technique may use a sheet of moldable material 22. The sheet of moldable material 22 may have a first end 23 and a second end 24. The sheet of moldable material 22 may be made of, for example, a thermoplastic material, a thermoset material or may be produced using any other method of fabrication technique.

The sheet of moldable material 22 may vary in, for example, thickness and durometers of hardness. Additionally, the sheet of moldable material 22 may be a combination of the stiff material 25 and the soft material 26. As illustrated by FIG. 3, the stiff material 25 may be, for example, located at the first end 23 of the moldable sheet 22 and the soft material 26 may be located at the second end 24 of the moldable sheet 22. The stiff material 25 may be used for the area of the dental appliance 1 where retention of the teeth is desired in their current position and the soft material 26 may be used in those areas requiring tooth correction or guidance.

If a high percentage of stiff material 25 is used in creating the dental appliance 1, there may be an increase in the retainability of the dental appliance 1. However, a high percentage of stiff material 25 in more areas of the dental appliance 1 may also increase the number of dental appliances 1 required and, therefore, increase the expense to the patient and length of treatment time. After the teeth are completely straightened, a dental appliance 1 having mostly and/or all stiff material 25 may be computer-generated by another final model of the teeth of the patient as a final retainer.

If the dental appliance 1 is created with a mixture of the stiff material 25 and the soft material 26, the dental appliance 1 may have good retainability in the stiff material 25 portion. The soft material 26 may accelerate the correction time required for tooth movement. However, the number of additional dental appliances 1 may be reduced. As a result, the amount of effort needed by a dentist or orthodontist is reduced and the patient may save money.

If the entire dental appliance 1 is constructed of the stiff material 25, and if erupting teeth are present, the teeth sockets 4 may not fit correctly onto the teeth of the patient. More specifically, the teeth sockets 4 may not fit once the teeth erupt slightly, thereby causing the eruption process to be slowed or stopped and/or the dental appliance 1 may not fit. As a result, the teeth sockets 4 may be altered anatomically to adapt to the change; however several additional dental appliances 1 may be required. If the predicted tooth area 12 is made of teeth sockets 4 in a soft material 26, the eruption may take place normally without the need for additional dental appliances 1.

The anatomy of the teeth, especially in the predicted tooth area 12 may be altered manually or by computer to adopt to, for example, racial differences such as shovel-shaped incisors common in people of Asian descent and the more square-shaped teeth common in people of African descent. Differences in teeth shape are illustrated in FIG. 6.

If the entire dental appliance 1 is constructed of soft material 26, the retainability may be reduced. Further, the number of dental appliances 1 needed may be reduced and the amount of time required by a dentist or orthodontist may also be reduced, thereby saving the patient money.

Referring now to FIG. 4A, the teeth sockets 4 may either be a single tooth slot 13 or a multiple tooth slot 14. The single tooth slot 13 may fit one tooth of the patient and the multiple tooth slot 14 may fit more than one tooth of the patient. The multiple tooth slot 14 may fit, for example, the second bicuspid and first permanent molar of a patient. More specifically, the multiple tooth slot 14 may fit the first and second deciduous molars and first permanent molar of the patient, for example, between the ages of eight and eleven. The multiple tooth slot 14 may be designed, for example, for the patient who does not have the adult second molars present distal to the V-V line, as seen in FIG. 4C. Further, the multiple tooth slot 14 may accommodate all of the teeth of the patient with no individual teeth sockets 4.

Referring now to FIG. 4B, the multiple tooth slot 14 may be designed, for example, to fit the first and second deciduous molars of the patient. More specifically, the multiple tooth slot 14 may be designed, for example, for a patient under the age of six years of age. However, the multiple tooth slot 14 may not have any slot for the first permanent molar distal to the W-W line. Additionally, the multiple tooth slot 14 may fit all of the teeth of the patient after the first permanent molars have erupted distal to the W-W line for children aged six to eleven, as illustrated in FIG. 4C. Additionally, the multiple tooth slot 14 may be designed where no permanent molars are present distal to the W-W line for patients under six years of age, as illustrated in FIG. 4D. Further, the multiple tooth slot 14 may fit the first permanent molars distal to the W-W line and/or including the second permanent molars distal to the V-V line, as illustrated in FIG. 4E.

When a patient is expected to lose deciduous teeth and/or have permanent teeth replace the deciduous teeth, the teeth sockets 4 may be predicted based on the sizes and shapes of the already-erupted permanent teeth of the patient and/or from group standards. In addition, if the patient has some permanent teeth which are unerupted or erupting at the time, the teeth sockets 4 may be predicted based on the sizes of already-erupted permanent teeth of the patient.

The entire dental appliance 1 may have teeth sockets 4 if all of or almost all of the permanent teeth have yet to erupt. The unerupted tooth or teeth or partially-erupted permanent tooth crown may be predicted from a digital or standard x-ray image. The entire dental appliance 1 may be based on predicted tooth sizes and shapes as well as the shape and size of the upper and lower arches of the patient and/or from group standards.

The dental appliance 1 may be created manually of by the computer. Additionally, the dental appliance 1 may have some areas formed by the computer as a replication of a portion of the dentition of the patient for retainability. The portion of the dentition of the patient used for retainability may remain stable during the period of incisal eruption.

A youth aged five to seven may be expected to have any number of the upper and/or lower permanent incisors erupted or in the process of eruption. In such a case, the dental appliance 1 may have one or more predicted tooth areas 12.

If all of the adult teeth of the patient are not in the mouth of the patient, certain areas may need to be predicted from the size and shape of the existing permanent teeth. Therefore, measurements of the first permanent molars and/or adult incisors may be necessary if present in the mouth. If no adult teeth are present in the mouth, the size of one or more incisors may be estimated from a digital or standard x-ray view by an intra-oral or panoramic radiograph. The computer-generated dental appliance 1 or manually created dental appliance 1 may be partly a replica of the cast of the patient and/or partly a prediction of the size and shape of the teeth expected to erupt into the mouth. In addition, the computer-generated dental appliance 1 or manually created dental appliance 1 may have the duplicated tooth area 11 and/or the predicted tooth area 12 made into cast(s) from which the dental appliance 1 or graduated dental appliances may be made. In either case, certain areas or groups of teeth may be combined into a single tooth slot 13 or a multiple tooth slot 14. Further, the dental appliance 1 may have one or more single tooth slots 13 and/or multiple tooth slots 14.

In the computer-generated dental appliance 1 intended for an individual aged four to seven, a determination may be made if crowding of the permanent teeth is anticipated following eruption or if sufficient room is present in the arch 17. Additionally, a determination may need to be made if an interproximal space 15 will eventually be present. The computer can accomplish such an arch length analysis based on a difference between the measurement of the widths of permanent teeth expected to erupt into the mouth and the amount of space available for the eruption of the teeth. An amount of anticipated increase in arch 17 due to normal, eruption may also be factored into the analysis.

If crowding is anticipated, the computer-generated model, dental appliance 1 or appliances may be enlarged approximately 1.5 mm. from lower deciduous canine-to-canine dimension while the lower adult centrals may be erupting. In addition, the computer-generated model, dental appliance 1 or appliances may be enlarged another 2.0 mm. while the lower adult laterals may be erupting. Further, similar arch 17 expansions may be incorporated into the posterior segments. For example, the arch 17 expansions may be slightly smaller. The dental appliance 1 may not be intended to expand the arch 17, but the dental appliance 1 must be large enough to allow for natural expansion as the incisors force their way into the arch 17. The expansion of the incisors may be accomplished as the incisors force their way into either the single tooth slot 13 or the multiple tooth slot 14.

If a close fit of the dental appliance 1 is desired and only deciduous teeth are in place, the computer-generated dental appliance 1 may duplicate only those teeth that will be in the mouth for at least enough time until another dental appliance 1 may be used or until the front adult incisors have fully erupted. If some deciduous teeth are expected to exfoliate within a short period, the predicted tooth area 12 and teeth sockets 4 may be formed by the computer. The teeth sockets 4 may be sized and/or shaped for the incoming permanent teeth which may replace the exfoliated deciduous teeth after the first permanent molars erupt.

Adjustments may need to be made to the dental appliance 1 to allow for the mesial drift that closes the leeway space. The leeway space may be the space created by the size difference between the wider deciduous posterior teeth and the narrower permanent teeth which replace them. To solve this, a dentist or orthodontist may provide a larger size of the dental appliance 1 to the patient which may allow for arch 17 expansion to take place. In addition, the dentist or orthodontist may provide the dental appliance 1 with the multiple tooth slot 14 instead of the single tooth slot 13.

The multiple tooth slot 14 may allow for certain areas, for example, the upper and/or lower posterior teeth to expand and also to adjust forward through the leeway space. To allow for eruption, especially of the posteriors during growth, less vertical inter-occlusal material 31 may need to be incorporated into the computer program. In addition, extra space may be provided in the occusal surface 37 while maintaining the fit around the gingival undercuts. The extra space may be needed, for example, to allow the teeth to be able to erupt properly. Further, the extra space may be needed, for example, to allow the teeth to erupt more completely during growth. At the same time, more material may be present in the anterior segment of the freeway space 31 which may aid in the correction of overbite.

In addition, alterations, such as a flattening of the occlusal surface 37 and/or the multiple tooth slot 14 of the posterior teeth may allow any tooth, regardless of the occlusal anatomy of the tooth to properly fit or erupt into the single tooth slot 13 or the multiple tooth slot 14 of the dental appliance 1. Additionally, the incisial edges 5 may be thinned to allow the teeth to erupt into the dental appliance 1 properly.

Furthermore, a similar situation may occur when the remaining adult teeth erupt when the patient is around ten years of age. It should be understood that the multiple tooth slot 14 may be provided instead of the single tooth slot 13. Further, the multiple tooth slot 14 may cover the entire dental appliance 1 and may be provided in one or several sizes.

Referring now to FIG. 5A, the dental appliance 1 may have the front end 27 (mesial), a back end 28 (distal), a top end 29 and a bottom end 30. Additionally, the dental appliance 1 may have material between the upper and lower teeth or within the freeway space 31. The amount of material at the front end 27 of the dental appliance 1 may be greater than the amount of material at the back end 28 of the dental appliance 1. In addition, the altered freeway space 31 may improve overbite corrections when the amount of the material is increased in the front end 27 of the dental appliance 1 and decreased in the back end 28 of the dental appliance 1.

Further, the altered freeway space 31 may aid in open-bite corrections if the alterations are reversed, wherein less of the material may be implemented in the front end 27 and more material may be implemented in back end 28. Still further, if the front end 27 of the dental appliance 1 is increased at the freeway space 31 and reduced in the back end 28, an overbite may be corrected. Additionally, if the freeway space 31 at the front end 27 is reduced and the freeway space 31 at the back end 28 is increased, an openbite may be corrected. Additionally, a slit (not shown) may be created between the upper and lower incisal edges 5 in the front end 27 which may correct, for example, openbite.

Figure 5B:
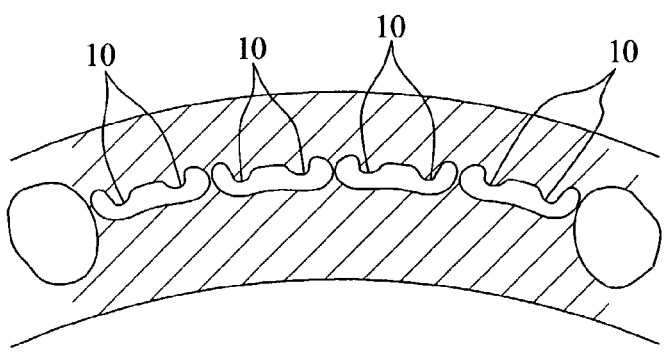
FIG. 5B illustrates a front view of the dental appliance of FIG. 5A having protruding ribs in an embodiment of the present invention.
Figure 5C:
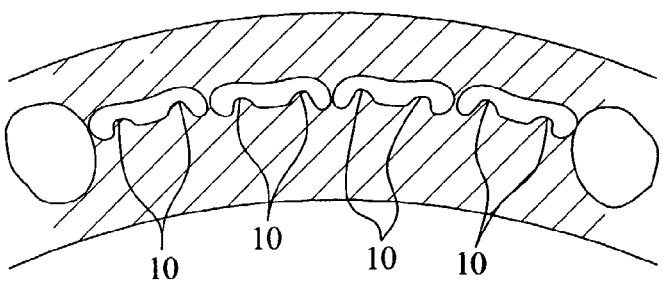
FIG. 5C illustrates a top view of the dental appliance of FIG. 5B in an embodiment of the present invention.
Figure 5E:
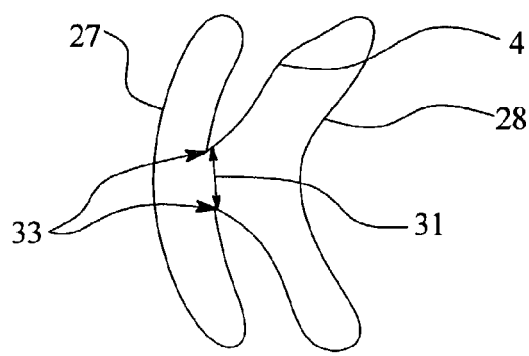
FIG. 5E illustrates a cross sectional view of incisal edges of the dental appliance of FIG. 5B in an embodiment of the present invention.

Referring now to FIGS. 5B, 5C and 5D, as mentioned above, protruding ribs 10 may be present in the teeth sockets 4 of the dental appliance 1. The protruding ribs 10 may aid in the rotation of the teeth of the patient into a desired position. In addition, the protruding ribs 10 may be present on the labial surface 8 and/or the lingual side 9 of the teeth sockets 4. In the alternative, bumps and/or elevations may be present in the teeth sockets 4 instead of the protruding ribs 10 to aid in the rotation of the teeth of the patient. FIG. 5E illustrates a cross-sectional view of the dental appliance 1. The tooth socket 4 of the dental appliance 1 may have the narrowed incisal edge 5.

Figure 6A:
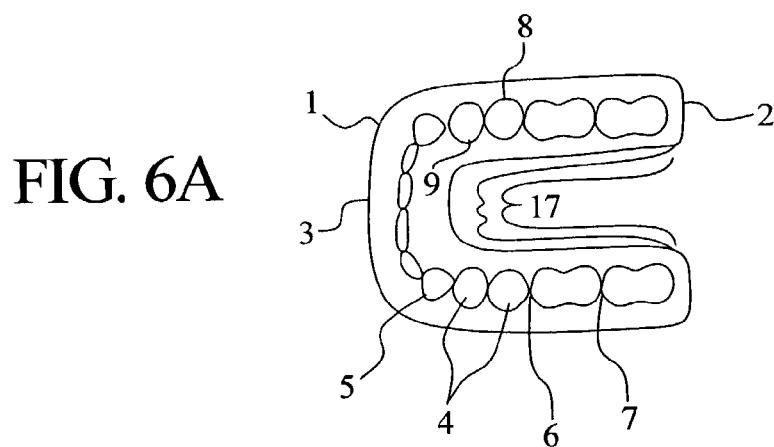
FIG. 6A illustrates a top plan view of a square type arch in a dental appliance in an embodiment of the present invention.
Figure 6B:
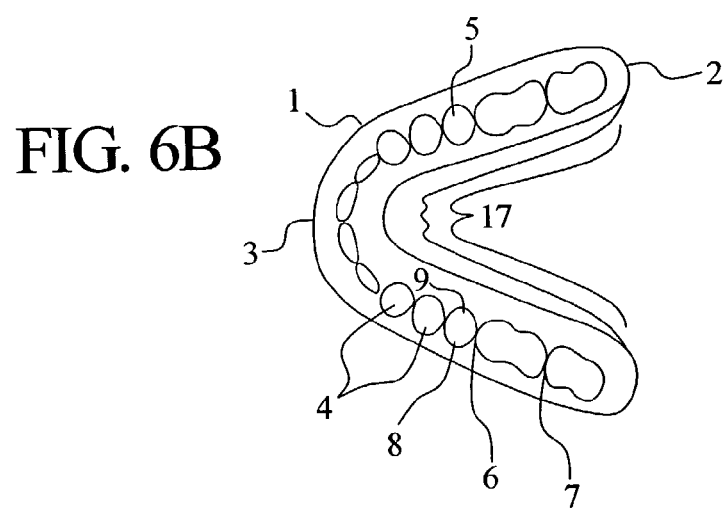
FIG. 6B illustrates a top plan view of a tapered type arch in a dental appliance in an embodiment of the present invention.

Referring now to FIGS. 6A and 6B, the natural arch of a patient may be generally square-like in shape. As a result, the dental appliance 1 may be altered to fit the square-like form of the arch of the teeth of the patient. Alternatively, the arch of the patient may be tapered. Accordingly, the dental appliance 1 may have a tapered arch 17 formed to fit a patient with a natural tapered arch.

Figure 6C:
FIG. 6C illustrates a cross section view of a shovel shaped type of an upper central incisor common in Asian people.
Figure 6D:
FIG. 6D illustrates an incisor common in Caucasian people.
Figure 6E:
FIG. 6E illustrates an incisor common in people of African descent.

FIG. 6C illustrates a cross-section of an upper central incisor 16 having a shape that is common to people of Asian descent. FIGS. 6D and 6E generally illustrate an alternate form of naturally occurring incisors 16. More specifically, FIG. 6D illustrates an incisor 16 common to Caucasian people, whereas FIG. 6E illustrates an incisor 16 common to people of African descent.

Figure 7A:
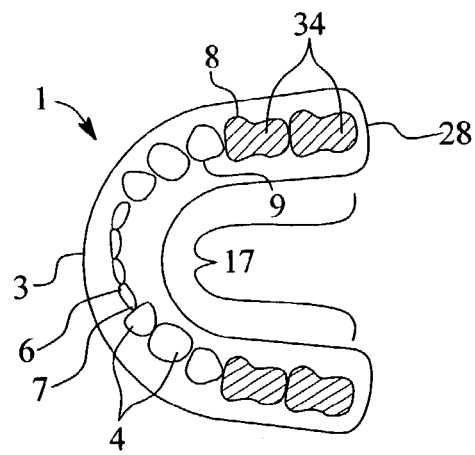
FIG. 7A illustrates a top plan view of a dental appliance in an embodiment of the present invention.
Figure 7B:
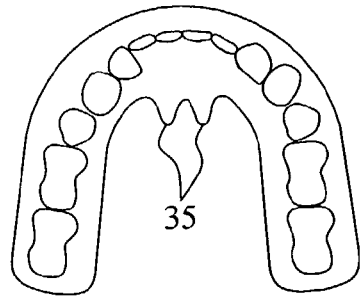
FIG. 7B illustrates a lower view of a dental appliance in an embodiment of the present invention.
Figure 7C:
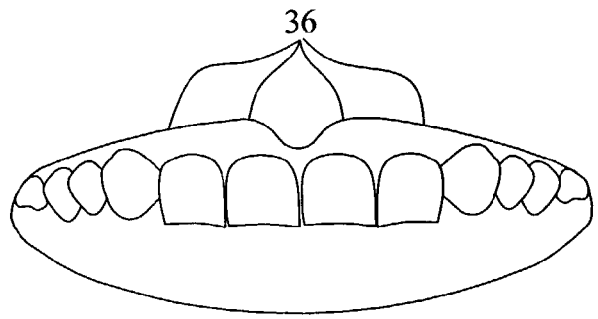
FIG. 7C illustrates a front sectional view of the teeth of a patient.
Figure 7D:
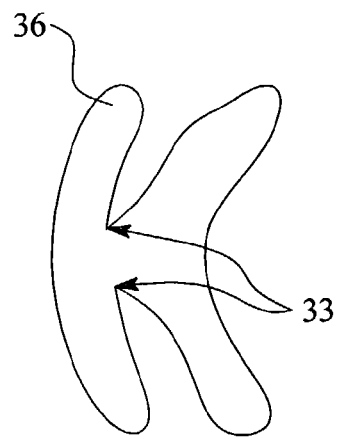
FIG. 7D illustrates a cross sectional view at the midline of the tooth of a patient.

Referring now to FIG. 7A, the dental appliance 1 may have a flattened portion 34 which may be at the occlusal surface 37 of the teeth sockets 4. FIG. 7B illustrates an upper view of a dental appliance in an embodiment of the present invention with lingual tabs 35. FIG. 7C illustrates a front sectional view of the teeth of a patient with the elevated labial shield 36. FIG. 7D illustrates a cross sectional view at the midline of the tooth of a patient with the narrowed incisal edge 5, 33.

It should be understood that various changes and modifications to the presently preferred embodiments described herein will be apparent to those skilled in the art. Such changes and modifications may be made without departing from the spirit and scope of the present invention and without diminishing its attendant advantages.

I claim:

1. A dental appliance adapted to be worn in a mouth of a user, the dental appliance comprising:

a generally U-shaped base having a length defined between a first end and a second end and further wherein the generally U-shaped base has a top surface and a bottom surface wherein the generally U-shaped base is sized to receive one or more teeth of a user when the generally U-shaped base is worn in the mouth of the user;

a first portion of the generally U-shaped base wherein the first portion has a first occlusal surface and at least two side walls adjacent to the first occlusal surface wherein the occlusal surface and the side walls adjacent to the first occlusal surface form a first interior shaped and sized to match a predicted shape and size of one or more teeth of the user which have not erupted wherein the first portion is constructed from a first material; and a second portion of the base wherein the second portion has a second occlusal surface and at least two side walls adjacent to the second occlusal surface wherein the occlusal surface and the side walls adjacent to the second occlusal surface form a second interior shaped and sized to match a shape and a size of one or more teeth of the user which have erupted wherein the predicted size of one or more teeth of the user which have not erupted is estimated from the size of one or more teeth of the user which have erupted into the mouth of the user wherein the second portion is constructed from a second material wherein the first material is softer than the second material wherein the first portion and the second portion are different distances from the first end.

2. The dental appliance of claim 1 further comprising:

a tab integrally formed with the base wherein the tab extends horizontally from the base into the mouth of the user when the generally U-shaped base is worn in the mouth of the user.

3. The dental appliance of claim 1 wherein a distance between the top surface and the bottom surface at the first end is greater than a distance between the top surface and the bottom surface at the second end.

4. The dental appliance of claim 1 further comprising:
a shield integrally formed with the base wherein the shield extends vertically from the base and is adapted to contact the teeth of the user when the generally U-shaped base is worn in the mouth of the user.

5. The dental appliance of claim 1 further comprising:
a socket within the base wherein the socket has a flat occlusal surface.

6. The dental appliance of claim 1 further comprising:
a rib integrally formed within the base wherein the rib protrudes from the first portion of the generally U-shaped base into the interior of the first portion toward at least one tooth wherein the rib contacts and rotates at least one tooth in the mouth of the user when the U-shaped base is worn in the mouth of the user.

7. The dental appliance of claim 1 further comprising:
a socket within the generally U-shaped base wherein the socket has a circumference that matches a circumference of at least two teeth of the user when the generally U-shaped base is worn in the mouth of the user.

8. A dental appliance adapted to be worn adjacent to teeth in a mouth of a user wherein the mouth of the user has one or more teeth which erupted into the mouth of the user, the dental appliance comprising:
a generally U-shaped base sized to receive one or more teeth of a user when the generally U-shaped base is worn in the mouth of the user wherein the base has a length defined by a first end and a second end;
first sockets for receiving one or more teeth when the generally U-shaped base is worn in the mouth of the user wherein the sockets are formed in the base and further wherein each of the sockets has walls and an occlusal surface connected to the occlusal surface wherein the walls and the occlusal surface define an interior having a circumference and a height computer-generated from a predicted size of one or more incisors of the user which have not erupted wherein the predicted size of the one or more incisors of the user is calculated from one or more teeth which erupted into the mouth of the user wherein the first sockets are manufactured from a first material; and
second sockets in the base wherein the second sockets receive the one or more teeth which erupted into the mouth of the user wherein the second sockets are manufactured from a second material wherein the second material is more rigid than the first material.

9. The dental appliance of claim 8 further comprising:
a shield integrally formed with the base wherein the shield has a shape which corresponds to a shape of the mouth and extends vertically from the base.

10. The dental appliance of claim 8 further comprising:
a tab integrally formed with the generally U-shaped base wherein the tab is adapted to extend horizontally into the mouth of the user when the generally U-shaped base is worn in the mouth of the user.

11. The dental appliance of claim 8 further comprising:
a rib integrally formed within the generally U-shaped base and protruding from the socket into the interior of the socket toward one of the teeth wherein the rib is adapted to contact said one of the teeth and is adapted to rotate the tooth of the user when the generally U-shaped base is worn in the mouth of the user.

12. The dental appliance of claim 8 wherein the occlusal surface of one of the first sockets within the base is a flat occlusal surface.

13. The dental appliance of claim 8 wherein one of the second sockets within the base has a flat occlusal surface.

14. A dental appliance adapted to be worn adjacent to teeth in a mouth of a user wherein one or more teeth of the user erupted into the mouth of the user, the dental appliance comprising:
a generally U-shaped base sized to receive one or more of the teeth of the user when the generally U-shaped base is worn in the mouth of the user;
a predicted socket formed within the generally U-shaped base wherein the predicted socket has walls and an occlusal surface shaped and sized to match a shape and a size of one or more teeth of the user which have not erupted wherein a spacing of the walls and the occlusal surface of the predicted socket is based on an image of an interior of a mouth of the user wherein the spacing of the walls and the occlusal surface of the predicted socket corresponds to the shape and the size of one or more teeth of the user which erupted into the mouth of the user wherein the predicted socket is constructed from a first material; and
a duplicated socket formed within the generally U-shaped base wherein the predicted socket has walls and an occlusal surface shaped and sized to match a shape and a size of one or more teeth of the user which have erupted wherein the duplicated socket is constructed from a second material and the first material is less rigid than the second socket.

15. The dental appliance of claim 14 wherein the image is an X-ray image.

16. The dental appliance of claim 14 wherein the image is a digital image.

17. The dental appliance of claim 14 further comprising:
a tab integrally formed with the generally U-shaped base wherein the tab is adapted to extend horizontally from the generally U-shaped base into the mouth of the user when the generally U-shaped base is worn in the mouth of the user.

18. The dental appliance of claim 14 further comprising:
a rib integrally formed within the socket of the generally U-shaped base wherein the rib protrudes from one of the walls of the socket toward the teeth of the user and contacts the teeth of the user at an end portion of the rib farthest from the wall of the socket to move the teeth of the user when the generally U-shaped base is worn in the mouth of the user.

19. A dental appliance adapted to be worn in the mouth of a user, the dental appliance comprising:
a generally U-shaped base sized to receive one or more teeth in the mouth of a user when the generally U-shaped base is worn in the mouth of the user; and
a first socket formed within the generally U-shaped base wherein the first socket has walls and an occlusal surface that form an interior wherein the interior matches a shape and a size of the single tooth of the user which has not erupted based on a predicted size of the single tooth wherein the predicted size is based on a size of two or more teeth of the user which erupted into the mouth of the user; and
a second socket formed within the generally U-shaped base wherein the second socket is sized and shaped to match a combined shape and a combined size of two or more teeth of the user which erupted into the mouth of the user when the generally U-shaped base is worn in the mouth of the user wherein the first socket is constructed from a first material, the second socket is constructed from a second material and the first material is softer than the second material.

20. The dental appliance of claim 19 further comprising:
a tab integrally formed with the generally U-shaped base wherein the tab is adapted to extend horizontally into the mouth of the user when the generally U-shaped base is worn in the mouth of the user.

21. The dental appliance of claim 19 further comprising:
a shield integrally formed with the generally U-shaped base wherein the shield extends vertically from the generally U-shaped base and covers the teeth of the user when the generally U-shaped base is worn in the mouth of the user.

22. The dental appliance of claim 19 wherein the base is constructed from the first material and the second material.

23. A dental appliance adapted to be worn in a mouth of a user wherein the user has a tongue within the mouth of the user wherein the mouth of the user has one or more teeth which erupted into the mouth of the user, the dental appliance comprising:
a generally U-shaped base sized to receive teeth in a mouth of a user when the generally U-shaped base is worn in the mouth of the user; and
a first socket formed within the generally U-shaped base wherein the first socket has an occlusal surface, a labial wall and a lingual wall defining an interior wherein the interior is sized and shaped to receive one or more teeth of the user when the generally U-shaped base is worn in the mouth of the user wherein the lingual wall is adjacent to the tongue of the user and further wherein the first socket has a rib integrally formed within the first socket wherein the rib extends from the first socket into the interior of the first socket wherein the rib projects toward one or more of the teeth of the user when the generally U-shaped base is worn in the mouth of the user wherein a portion of the rib farthest from the first socket contacts the tooth and rotates the tooth wherein the base is constructed from a first material and the first socket is constructed from a second material wherein the second material is softer than the first material.

24. The dental appliance of claim 23 wherein the size of the generally U-shaped base is based on a predicted size of a tooth which has not erupted wherein the predicted size of the tooth which has not erupted corresponds to one or more teeth of the user which erupted into the mouth of the user.

25. The dental appliance of claim 23 further comprising:
a tab that extends horizontally from the base and is integrally formed with the generally U-shaped base wherein the tab has an apex.

26. The dental appliance of claim 23 further comprising:
a second socket formed in the base wherein the second socket is constructed from the first material.

27. The dental appliance of claim 23 further comprising:
a shield integrally formed with the generally U-shaped base wherein the shield extends vertically from the generally U-shaped base and contacts the teeth of the user when the generally U-shaped base is worn in the mouth of the user.

28. A dental appliance worn adjacent to teeth of a user in a mouth of the user, the dental appliance comprising:
a generally U-shaped base;
a first socket formed within the generally U-shaped base wherein the first socket has walls and an occlusal surface wherein a spacing of the walls from the occlusal surface matches a shape and a size of the socket to a shape and a size of one of the teeth of the user which erupted into the mouth of the user wherein the first socket is constructed from a first material; and
a second socket formed within the generally U-shaped base wherein the second socket receives two or more teeth of the user when the generally U-shaped base is worn in the mouth of the user wherein the second socket has a flat surface which is adapted to contact the teeth when the generally U-shaped base is worn in the mouth of the user and further wherein the second socket is shaped and sized based on a predicted shape and size of at least one tooth of the user which has not erupted wherein the predicted shape and size is estimated from the shape and the size of one of the teeth of the user which erupted into the mouth of the user wherein the second socket is constructed from a second material wherein the first material is softer than the second material.

29. The dental appliance of claim 28 wherein the base is constructed from the second material.

30. The dental appliance of claim 28 wherein the base is constructed from the first material.

31. The dental appliance of claim 28 further comprising:
a rib integrally formed within the first socket and protruding from one of the walls of the first socket toward the tooth of the user wherein an end portion of the rib farthest from the wall of the first socket contacts the tooth of the user and rotates the tooth of the user when the generally U-shaped base is worn in the mouth of the user.

32. A dental appliance adapted to be worn adjacent to teeth in a mouth of a user wherein the user has a lip adjacent to the mouth of the user wherein the user has a tongue in the mouth of the user, the dental appliance comprising:
a generally U-shaped base having a first end, a second end, an inside perimeter and an outside perimeter wherein the first end is located in a position opposite to the second end wherein the base has a length defined by the first end and the second end;
a wall extending from the base along the outside perimeter wherein the wall has a labial surface and a lingual surface wherein the wall has one or more protrusions extending from the labial surface inwardly with respect to the inside perimeter of the generally U-shaped base wherein the labial surface is adjacent to the lip of the user wherein the lingual surface is adjacent to the tongue of the user wherein the labial surface and the lingual surface are spaced from each other based on the size and the shape of a tooth of the user wherein one or more protrusions contact and rotate the tooth of the user when the generally U-shaped base is worn in the mouth of the user wherein the wall has a first portion and a second portion wherein the first portion and the second portion are different distances from the first end of the base and further wherein the first portion is constructed from a first material and the second portion is constructed from a second material wherein the first material is softer than the second material.

33. The dental appliance of claim 32 further comprising:
a tab integrally formed within the base wherein the tab is adapted to extend horizontally into the mouth of the user when the generally U-shaped base is worn in the mouth of the user.

34. The dental appliance of claim 32 further comprising:
a rib integrally formed within the lingual surface of the base wherein the rib protrudes outward from the lingual surface of the base toward the tooth wherein an end portion of the rib farthest from the lingual surface contacts and moves the tooth of the user when the generally U-shaped base is worn in the mouth of the user.

35. The dental appliance of claim 32 further comprising:
a socket formed within the generally U-shaped base wherein the socket has an occlusal surface and walls wherein a labial wall is adjacent to the lip of the user and a lingual wall is adjacent to the tongue of the user wherein the labial wall, the lingual wall and the occlusal surface form an interior shaped and sized to match the shape and the size of at least one of the teeth of the user when the generally U-shaped base is worn in the mouth of the user.

36. The dental appliance of claim 32 further comprising:
a socket formed within the generally U-shaped base wherein the socket has an occlusal surface, a mesial wall and a distal wall that form an interior wherein the socket is shaped and sized to match the shape and the size of at least one of the teeth of the user when the generally U-shaped base is worn in the mouth of the user.

37. The dental appliance of claim 32 wherein the base is sized based on a predicted size of a tooth which has not erupted.

38. The dental appliance of claim 32 wherein the base is constructed from the first material.

39. A U-shaped dental appliance adapted to correct a malocclusion in a mouth of a user having a generally U-shaped base wherein the base has a duplicated tooth area which suppresses movement of one or more teeth of the user and a predicted tooth area which is adapted to guide tooth movement of one or more teeth of the user wherein the duplicated tooth area has one or more sockets made of stiff material and correspond to the erupted teeth of the user and the predicted tooth area has one or more sockets made of soft material wherein the soft material is adapted to move one or more teeth of the user when the generally U-shaped base is worn in the mouth of the user wherein each socket has walls that define a socket circumference and a socket height that matches a tooth circumference and a tooth height of one or more teeth of the user.

40. The U-shaped dental appliance of claim 39 wherein the soft material is rubber.

41. The U-shaped dental appliance of claim 39 additionally comprising lateral tabs for advancing the lower jaw and increasing the growth of the lower jaw.

42. The U-shaped dental appliance of claim 39 additionally comprising an elevated labial shield extending vertically from a labial side of the generally U-shaped base wherein the labial shield advances the lower jaw of the user when the U-shaped dental appliance is worn in the mouth of the user.

43. The U-shaped dental appliance of claim 39 wherein one or more of the tooth sockets in the duplicated tooth area are multiple tooth slots.

44. The U-shaped dental appliance of claim 39 wherein one or more of the tooth sockets in the predicted tooth area are multiple tooth slots.

45. The U-shaped dental appliance of claim 39 further comprising:
a rib integrally formed within the predicted area of the generally U-shaped base and protruding from the predicted area of the generally U-shaped base towards one or more teeth of the user within the predicted area wherein the rib contacts one or more teeth of the user within the predicted area of the generally U-shaped base and moves the one or more teeth of the user contacted by the rib when the generally U-shaped base is worn in the mouth of the user.

46. The U-shaped dental appliance of claim 39 further comprising:
a rib integrally formed within a non-predicted tooth area of the generally U-shaped base and protruding from the non-predicted tooth area of the generally U-shaped base towards one or more teeth of the user wherein the rib contacts and moves one or more teeth within the predicted area of the generally U-shaped base when the generally U-shaped base is worn in the mouth of the user.

47. The U-shaped dental appliance of claim 39 further comprising:
a freeway space adjacent to the first portion and the second portion of the generally U-shaped base wherein the freeway space increases in thickness in a rearward direction.

48. A kit comprising at least two U-shaped dental appliances adapted to be worn on teeth of a user in a mouth of the user for correcting a malocclusion of the teeth in the mouth of the user wherein the mouth of the user has one or more erupted teeth, each appliance has a duplicated tooth area which is adapted to suppress movement of one or more teeth of the user wherein the duplicated tooth area is determined from one or more erupted teeth of the user and a predicted tooth area which is adapted to guide tooth movement of one or more teeth of the user wherein the duplicated tooth area has one or more sockets made of stiff material and the predicted tooth area has one or more sockets made of soft material wherein one or more sockets in the predicted tooth area is computer-generated from one or more erupted teeth of the user.

* * * * *